United States Patent [19]
Kleditsch et al.

[11] Patent Number: 5,470,349
[45] Date of Patent: Nov. 28, 1995

[54] DEVICE FOR TREATING INFLAMMATORY SKIN CHANGES IN THE INITIAL STAGE, AND METHOD FOR USING SAME

[75] Inventors: Bernhard Kleditsch, Berlin; Gabriel Khazaka, Köln, both of Germany

[73] Assignee: Courage & Khazaka Electronic GmbH, Köln, Germany

[21] Appl. No.: 162,154

[22] PCT Filed: Jun. 16, 1992

[86] PCT No.: PCT/EP92/01361

§ 371 Date: Mar. 22, 1994

§ 102(e) Date: Mar. 22, 1994

[87] PCT Pub. No.: WO92/22349

PCT Pub. Date: Dec. 23, 1992

[30] Foreign Application Priority Data

Jun. 18, 1991 [DE] Germany .......................... 41 20 517.0

[51] Int. Cl.[6] .................................................. A61N 1/20
[52] U.S. Cl. .................................. 607/75; 607/150
[58] Field of Search ............................. 607/62, 63, 75, 607/145, 150, 151, 153; 604/21

[56] References Cited

U.S. PATENT DOCUMENTS

| | | | |
|---|---|---|---|
| 712,220 | 10/1902 | Vetter et al. | 607/151 |
| 2,659,372 | 11/1953 | Andresen | 607/151 |
| 2,994,324 | 8/1961 | Lemos | 607/151 |
| 4,323,073 | 4/1982 | Ferris | 607/75 |
| 4,406,658 | 9/1983 | Lattiw et al. | 607/75 |

FOREIGN PATENT DOCUMENTS

| | | | |
|---|---|---|---|
| 158336 | 4/1984 | European Pat. Off. . | |
| 1450733 | 7/1965 | France . | |
| 74 12143 | 4/1974 | France . | |
| 186177 | 7/1965 | Germany . | |
| 2304533 | 1/1973 | Germany . | |
| 3719353 | 12/1988 | Germany . | |
| 0021279 | 9/1906 | Sweden | 607/145 |
| 0513526 | 10/1939 | United Kingdom | 607/145 |
| 2115700 | 10/1982 | United Kingdom . | |

*Primary Examiner*—William E. Kamm
*Attorney, Agent, or Firm*—Keil & Weinkauf

[57] ABSTRACT

This device for treating skin conditions with galvanotherapy features a DC power supply, one pole of which is connected to a central pin electrode. The other pole is connected either to several counter-electrodes arranged around the central electrode, or to a single counter-electrode shaped to surround the electrode. The electrode and counter-electrode(s) are pressed against the skin, and power is applied to them, treating the area of skin within the pattern defined by the counter-electrode(s) with galvanotherapy. It is possible to treat various sizes and patterns of skin conditions by specifying an appropriate counter-electrode pattern.

20 Claims, 6 Drawing Sheets

DEVICE FOR TREATING INFLAMMATORY SKIN CHANGES IN THE INITIAL STAGE, AND METHOD FOR USING SAME

The present invention relates to a device for treating inflammatory skin changes in the initial stage with the aid of electric direct current.

Appliances which use electric direct current for the therapeutic and cosmetic treatment of parts of the skin are known in principle. Thus, in utility model DE-G 90 17 597.2 there is an appliance for iontophoresis, in particular for the cosmetic treatment of parts of the face with direct-current source, liquid-moistened treatment electrode and hand electrodes, the treatment electrode and the hand electrode being connected electrically to the direct-current source. On the treatment electrode active substances of similar charges, which are present in aqueous solution or have been applied as ointment to the skin, are channeled into the skin by application of direct voltage.

In GB-A-2 064 178 an electrical supply unit is described for an appliance for silver ion therapy. In this case a positive layer polarized silver electrode is arranged directly on the parts of the tissue of the patient which is to be treated. The counter-electrode is secured at another position on the body. By switching on the direct current, silver ions on the silver-containing electrode connected as anode are released, which silver ions can penetrate through the tissue to be treated up to a depth of 1 cm, and their bactericidal action is made use of in the treatment.

Other appliances whose action is not based on the channelling of active substances into the tissue to be treated are likewise known. Thus, in GB-A-2 181 056 an appliance is described for the treatment of inflammatory skin changes, particularly in the mouth cavity. The appliance consists of a housing, which comprises a direct-current source, for example a battery, as well as a treatment electrode. The treatment electrode can be connected directly to the housing via an electrode carrier, in this case a clip then serves as counter-electrode, which clip is connected via a flexible cable to the current supply in the housing and can be arranged, for example, on the earlobe of the patient. As an alternative to this, the treatment electrodes can be connected via a cable to the direct-current source in the housing, the housing which the patient holds in his hand then serving itself as counter-electrode.

This appliance is noted for the fact that it is not very user-friendly, particularly in the case of self-treatment by the patient. In addition, only a very punctiform treatment of diseased skin areas is possible with this appliance, as a function of the limited electrode radius.

A device for galvanotherapy is known from the Swiss Patent Specification No. 65 020, which device comprises a housing, with a direct-current source fitted therein, and an electrode carrier on which are arranged at least two electrodes of opposite polarity, which electrodes are connected electrically to the direct-current source. The electrode carrier is in this case connected in a fixed manner to the housing. The two electrodes can have various shapes, the electrode and counter-electrode however being arranged parallel to one another in principle, as a result of which the area of skin to be treated is flanked by the electrodes (from two sides).

GB-A-21 15 700 describes a device for treating pains using a treatment electrode which is mounted on a spring and is movable in the longitudinal direction in the housing. The counter-electrode in this case concentrically circumscribes the housing in the grip part.

DE-A-37 19 353 discloses an electrical stimulator for nerves, whose stimulator circuit equipped with current stabilizer can be applied to the patients by means of an adhesive skin electrode and an electrically conducting puncture needle electrode, which is however insulated on the outside as far as the tip, a current intensity preselector with current intensity indicator for adjusting constant current intensities for the puncture procedure and nerve search procedure and a current intensity indicator being provided.

The object of the present invention is therefore to provide a device for treating inflammatory skin changes in the initial stage, with which device the disadvantages of the stated prior art are avoided. In addition, the device is to be manageable and simple to operate, so that the patient can carry it around and can also perform self-treatment at any time.

This object is achieved by a device for treating inflammatory skin changes in the initial stage, which device comprises a housing, with a direct-current source fitted therein, and an electrode carrier on which are arranged at least two electrodes of opposite polarity, which electrodes are connected electrically to the direct-current source, characterized in that a pin-shaped electrode is concentrically surrounded by one or more counter-electrodes, the electrode carrier being mounted movably on a spring in a cylindrical housing part, and the inner pin electrode being mounted on a spring inside the electrode carrier, the restoring force of which spring is less than that of the first spring, so that the electrode and the counter-electrode in the operating state of the device bear on the area of skin which is to be treated.

The direct-current source used is preferably a block battery, as a result of which the patient can carry the appliance around everywhere. However, in the case of a stationary treatment, it is also possible to connect the appliance directly to the mains supply via a power unit.

In addition, the device can have a switch and control unit with indicator facility for checking the charge state of the battery and the operating state of the device, as well as an adjustment facility for the operating voltage or the operating current. A suitable indicator facility can be, for example, a trio LED signal lamp which indicates the charge state of the battery when the battery test switch is activated.

If the battery charge is sufficient, the trio LED signal lamp then lights up in one color, for example red. At the same time, the trio LED signal lamp also serves as indicator display for the operating state of the device. With the electric switchout closed, the signal lamp lights up in another color, for example green, the brightness increasing as a function of the current flowing through the electrodes.

Alternatively, two independent indicator lamps or else acoustic signal transmitters can also be used.

The choice of the suitable operating voltage for the device depends to a great extent on the sensitivity of the area of skin to be treated. For this reason, an adjustment facility for the operating voltage is provided, which can be a changeover switch with which the voltage can be preset to 9 or 18 volts. Alternatively, a continuous adjustment of the operating voltage between 3 and 18 volts or of the operating current is also possible.

The electrodes of the device according to the invention should consist of a corrosion-resistant material which can be easily sterilized and disinfected. Special steel, noble metals and alloys of noble metals have proven particularly suitable.

The essential feature of the present invention lies in the special arrangement of the electrodes relative to one another, according to which one pin electrode is concentrically surrounded by one or more counter-electrodes. This concentric arrangement of electrode and counter-electrode has the advantage that the area of skin to be treated is completely enclosed between anode and cathode, as a result of which the whole area is permeated by current.

This electrode arrangement can be realized by various embodiments.

In a preferred embodiment the device comprises two electrodes, one electrode consisting of a straight pin, and the counter-electrode arranged parallel thereto consisting of a wire whose part bent at a right angle is designed as a wire loop which concentrically surrounds the first electrode. The wire loop can in this case have a very wide variety of geometries, such as, for example, the shape of a circle (16), an ellipse (29) or a polygon (29) having 3, 4, 5 or 6 corners. The diameter of the circle or of an outer circle which encloses the ellipse or the polygon can be varied according to the size of the area of skin which is to be treated. A diameter in the range between 5 and 15 mm, preferably between 8 and 10 mm, has proven expedient. In the preferred embodiment, the wire loop has the shape of a circle, the tip of the pin electrode and the wire ring of the counter-electrode lying in a common plane.

Alternatively, the electrode arrangement according to the invention can also be achieved by means of the device comprising two electrodes, where one electrode consists of a straight pin which is concentrically surrounded by a cylindrical counter-electrode (30).

Here too, a diameter of between 5 and 15 mm has proven expedient for the cylindrical electrode.

Alternatively, however, the device can also comprise a number of pin-shaped electrodes, where one electrode is arranged centrally on the electrode carrier and is concentrically surrounded by three to eight counter-electrodes which form the corners of a polygon. Four or six electrodes preferably surround the inner pin electrode. The distance between the outer and the inner pin electrode lies in the range between 5 and 15 mm.

The embodiments of the device according to the invention which have been described hitherto permit the treatment of a spatially limited area of skin, as a function of the distance between the central electrode and the counter-electrode(s) surrounding it. For the treatment of larger areas of skin, the device can be correspondingly modified.

In a preferred embodiment of the device according to the invention, the electrode carrier is arranged in a cylindrical housing part which is either integrated into the housing, which comprises the direct-current source, or is designed in the form of a pen and is connected electrically to the first housing via a flexible cable. The electrode carrier is mounted on a spring and is movable in the longitudinal direction in the cylindrical housing part and can be pushed inwards into the housing counter to the restoring force of the spring, as a result of which a switch which closes the circuit to the electrodes is activated. In addition, the inner pin electrode is mounted on a spring inside the electrode carrier, the restoring force of which spring is smaller than that of the first spring for the whole electrode carrier. In this case the tip of the central electrode protrudes beyond the concentric electrode ring surrounding it, regardless of whether the ring is formed by a wire loop, a cylinder or a plurality of pin-shaped counter-electrodes.

When the electrodes are applied to the area of skin to be treated, the central pin electrode therefore touches the skin first and is then pressed inwards counter to the restoring force of the spring, on which it is mounted in the electrode carrier, until the counter-electrode(s) also make(s) contact with the skin. As a result the distance between central electrode and counter-electrode is variable and can adapt to an unevenness of the skin. By firmer pressing of the electrodes onto the area of skin to be treated, the electrode carrier is pushed inwards into the cylindrical housing part counter to the restoring force of the first spring, as a result of which a switch is activated which closes the circuit to the electrodes. The mounting of the central electrode on a spring of smaller restoring force also ensures that the force with which the central electrode is pressed onto the area of skin is substantially less than the force with which the outer electrode(s) bears on the skin. This is particularly important since the central electrode has a smaller bearing surface than the counter-electrode(s) surrounding it. As a result the pressure of the central electrode on the area of skin to be treated is reduced, which means an additional treatment comfort for the patient, particularly in the case of painful skin changes. The device according to this preferred embodiment can also comprise a switch for reversing the polarity of the electrodes, which switch is integrated in the switch and control unit.

The cylindrical housing part is additionally designed such that the electrode carrier can be removed in a simple manner and can thus be easily replaced by electrode carriers with other electrode shapes or dimensions or can be disinfected and sterilized.

Skin areas in a state of incipient inflammation (serous phase) can be treated with the device described above. Examples of this are herpes, labialis, solitary skin eruptions of the neurodermatitis, insect bites.

An existing itching disappears immediately after the current application. This can be used, for example, in allergology following intracutaneous whealing of a substance, as a result of which a strong itching is generally caused.

In the treatment of an affected skin area, the following steps are carried out.

First, the charge state of the battery is checked and the operating voltage of the appliance is preset as a function of the area of the skin to be treated. Thereafter, the area of skin to be treated is moistened intensively with an electrolyte solution in order to permit a current flow between the electrode and counter-electrode.

Suitable electrolyte solutions are, for example, physiological saline solution, saliva or else water. The electrodes are then placed onto the moistened area of skin and the current flow is switched on. The treatment is continued until a first tingling sensation becomes noticeable on the area of skin to be treated.

Without wishing to give a complete theory on the mechanism of action of a direct-current treatment, attention is drawn to the fact that the change in the pH value around the electrodes as a result of electrolysis of the electrolyte solution plays a role in this.

This change in pH value not only occurs on the surface of the skin, but can also be observed within the indermal layer. This change in pH value prevents a further spreading of the pathogens of inflammation, and this explains why this treatment method can be used very successfully in particular in the initial stage of inflammation.

An advantage of the advice according to the invention also lies in their small overall dimensions and in the simple operation.

Thus, for example, a patient who is sensitive to herpes libiales can carry the appliance around at all times and immediately begin treatment directly upon the first appreciable tingling and incipient feeling of tension of the affected skin, regardless of where he is at the time.

The feeling of tension and the accompanying pain sensation immediately subsides, and the disease recedes completely within a few hours. The patient remains free from the vesicles and scab formation on the herpes labiales wound and the unpleasant consequences of restricted movement of the lips and the risk of the wound healing being delayed by bursting or tearing of the scab, and also from a possible secondary infection.

The various embodiments of the present invention are now explained in greater detail with reference to drawings.

Figure 8:
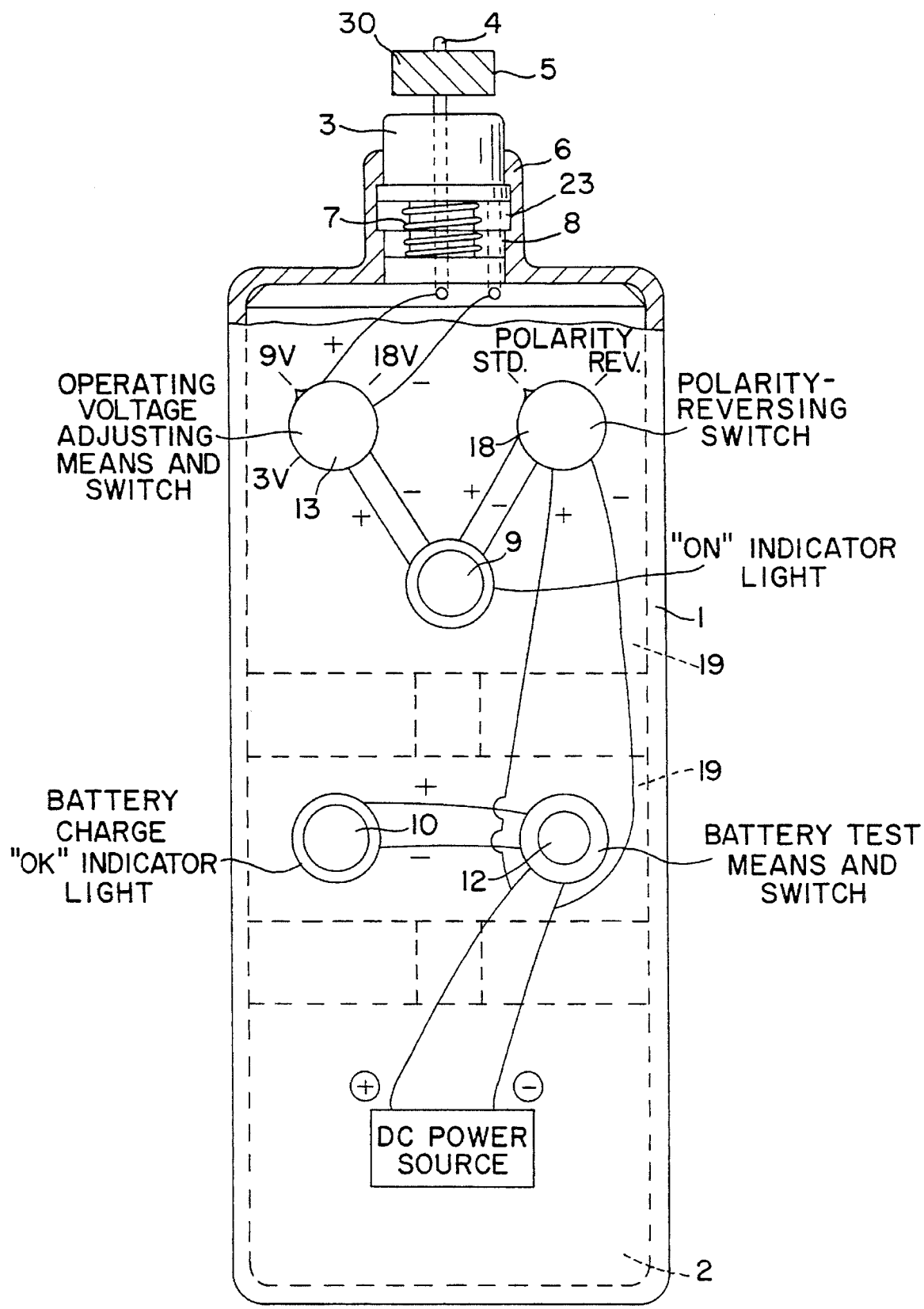

FIG. 8 shows the device with the DC power source (2), battery test means and switch (12), battery charge "OK" indicator light (10), polarity-reversing switch (18), operation indicator light (9), operating voltage adjusting means and switch (13) and cylindrical counter-electrode (30), as well as electrical connections from the power source through the various switches, etc., to the electrode and counter-electrode.

Figure 9:
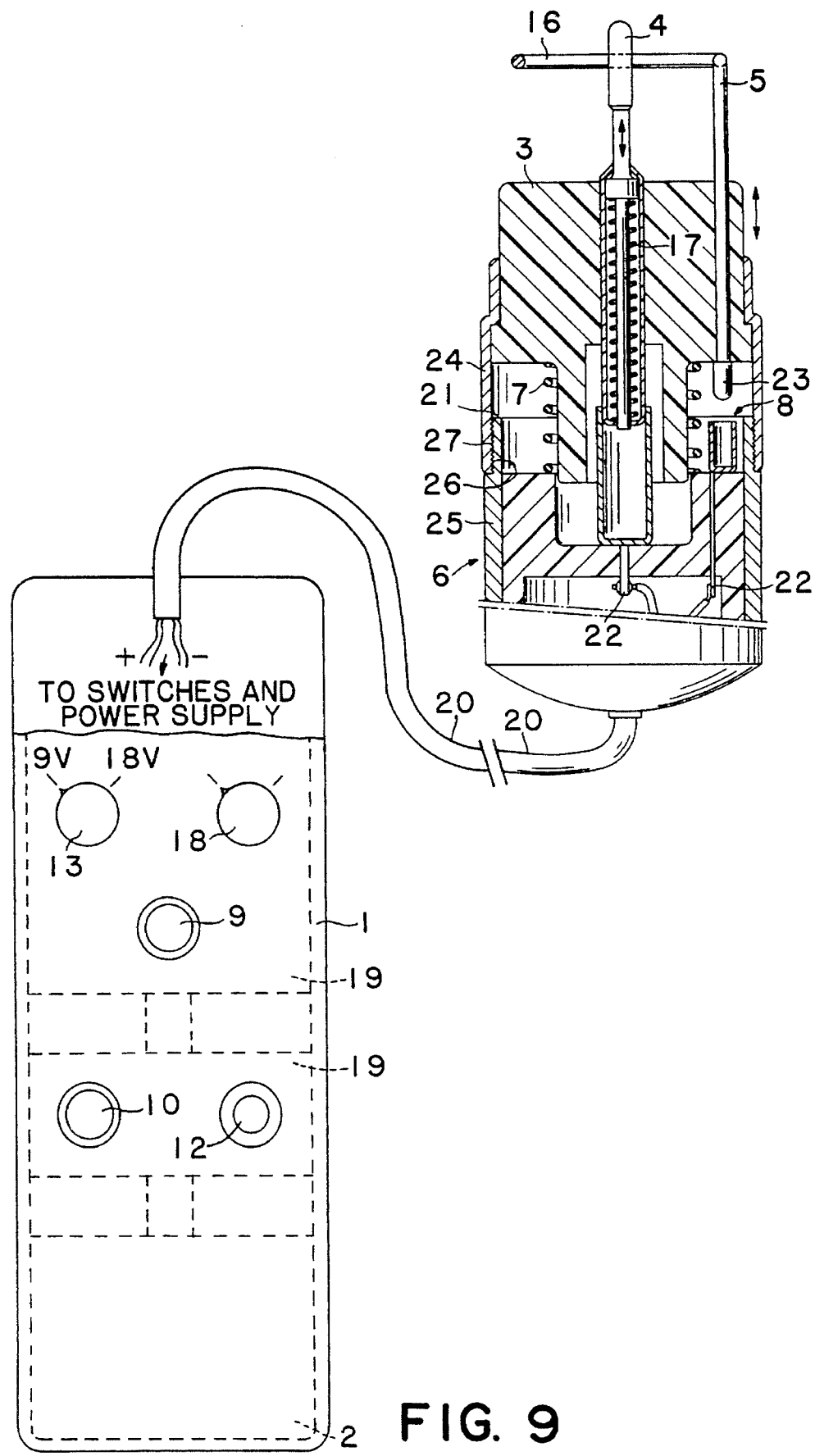

FIG. 9 shows an embodiment with a pen-shaped cylindrical housing part (6) containing the electrode carrier (3) being separate and electrically connected to the housing (1) by a flexible cable (20).

Figure 1:
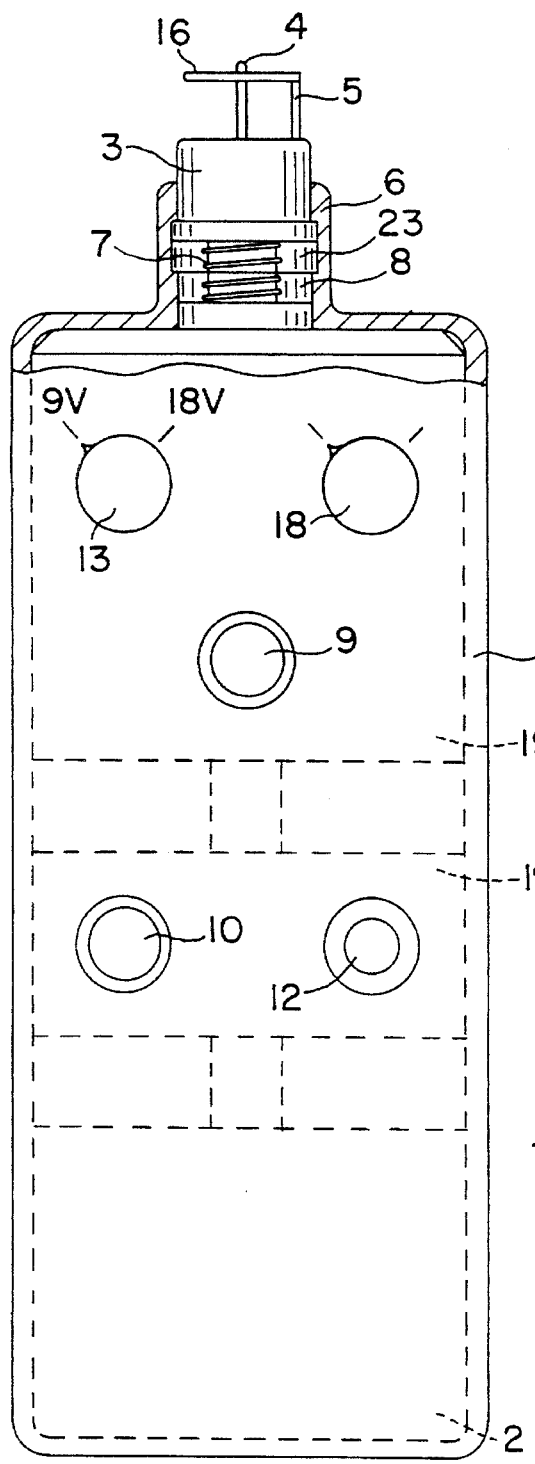
FIG. 1 shows the preferred embodiment of the present invention in a diagrammatic representation.

As can be seen from FIG. 1, the preferred embodiment of the device according to the invention comprises a housing 1 in which a direct-current source 2, such as, for example a battery, and also a switch and control unit 19 are arranged.

The switch and control unit 19 comprises a battery test switch 12 and a signal facility 10 which indicates the charge state of the battery upon activation of the battery test switch. This signal facility 10 can be either an indicator lamp or an acoustic signal transmitter.

The switch and control unit 19 furthermore comprises a voltage selector switch 13 in the form of a change-over switch with which the operator voltage can be preset to 9 or 18 volts, a pole change switch 18 with which the polarization of the two electrodes 4, 5 can be interchanged, and a display device 9 which can be either an indicator lamp or acoustic signal transmitter and which responds when the current flows through the two electrodes 4, 5. In this case the brightness of the indicator lamp or the loudness of the acoustic signal increases in proportion to the current flow.

The electrode carrier 3 is encountered in a cylindrical housing part 6 and is mounted on a spring 7. The cylindrical housing part 6 can either be connected directly to the housing 1, as shown in FIG. 1, or can be separate from the main housing 1, as represented in FIG. 3, and connected to the switch and control units 19 in the housing 1 via a flexible connection cable.

Figure 2:
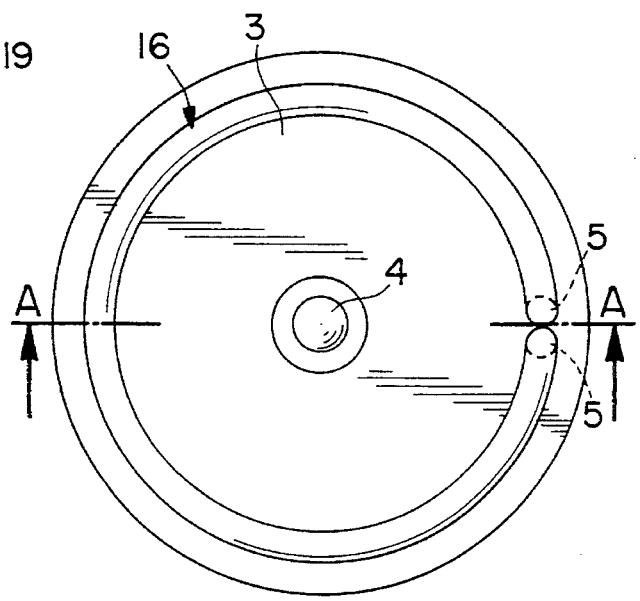
FIG. 2 shows the electrode carrier with the preferred electrode arrangement in cross-section from above.

As can be seen from FIG. 2, the preferred embodiment has two electrodes, one electrode 4 consisting of a straight pin which is arranged centrally in the electrode carrier 3, and the counter-electrode 5 parallel thereto consisting of a wire whose part bent at a right angle is designed as a wire ring 16 which concentrically surrounds the first electrode 4.

Figure 3:
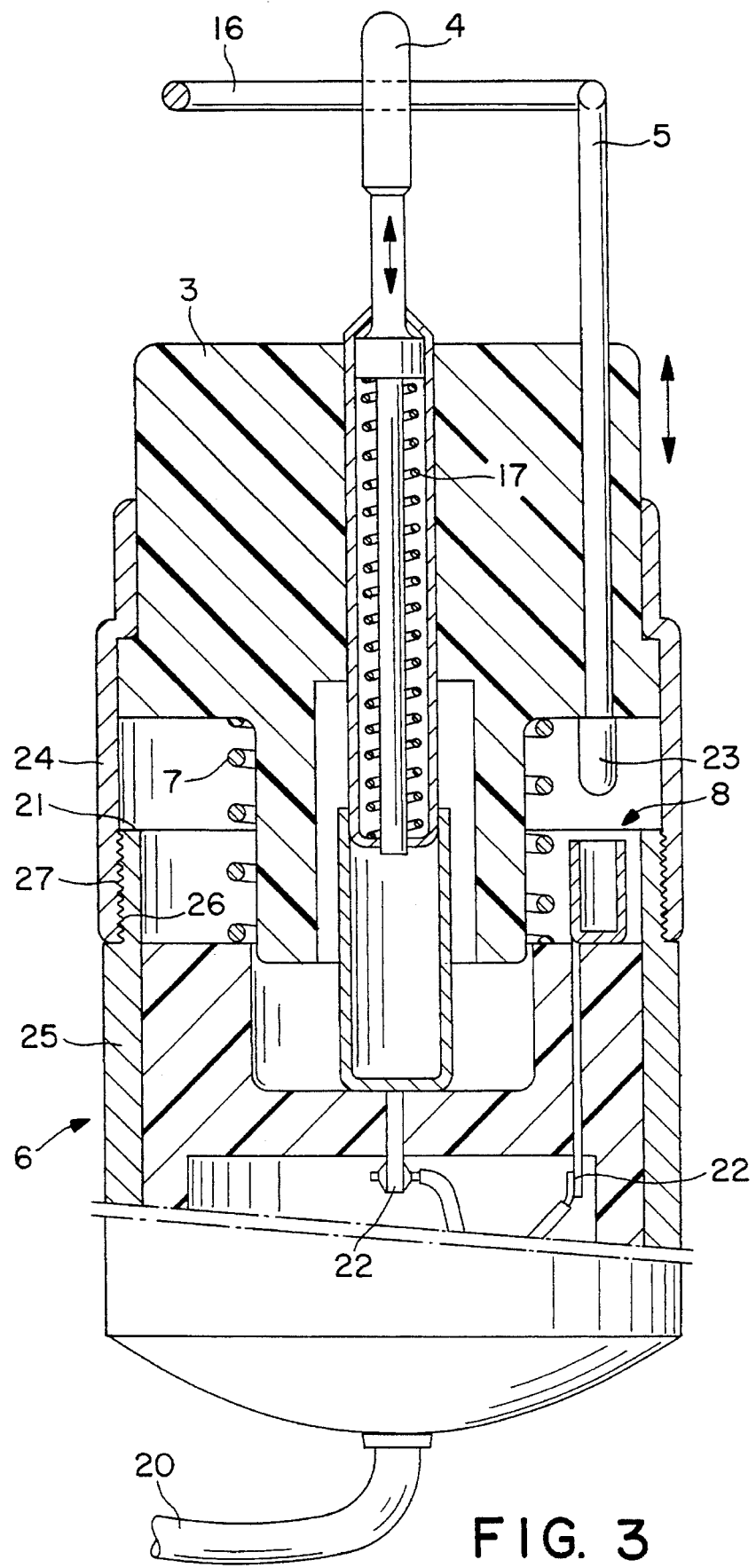
FIG. 3 shows the arrangement of the electrode carrier in the housing in a partial section along the line AN in FIG. 2.

As can be seen from FIG. 3, the central electrode 4 is guided through the wire ring 16 of the counter-electrode 5 and is spring-mounted in the electrode carrier 3. The restoring force of this spring 17 is in this case less than the restoring force of the spring 7 on which the whole electrode carrier 3 is mounted inside the cylindrical housing part 6.

The two electrodes 4 and 5 are connected via connections 22 to the switch and control unit 19 of the housing 1.

FIG. 3 also shows the mode of functioning of the device. The device is placed with the electrodes 4, 5 onto the area of skin to be treated. The electrode 4 is in this case pressed inwards into the electrode carrier 3 counter to the restoring force of the spring 17 until both the wire ring 16 and also the tip of the electrode 4 bear on the area of skin to be treated.

The central electrode 4 preferably has in this case a thickened part, so that the pressure of the electrode on the area of skin, which may be painful, remains low. The spring-mounting of the central electrode 4 also has the advantage that unevenness of the skin can be compensated and it is always possible to ensure that both the tip of the electrode 4 and also the wire ring 16 of the counter-electrode 5 bear firmly.

By pressing more heavily on the electrodes, the electrode carrier 3 is pushed inwards into the cylindrical housing 6 counter to the restoring force of the spring 7 until it bears on the limit stops 21. The switch pin 23 thus engages in the switch 8, as a result of which the circuit to the electrodes is closed and the treatment current flows between the two electrodes.

For the purpose of a simple replacement of the electrode carrier 3, the cylindrical housing part 6 is subdivided into a top part 24 and a bottom part 25 which are in each case provided with corresponding threads 26, 27 and are screwed together.

Figure 4:
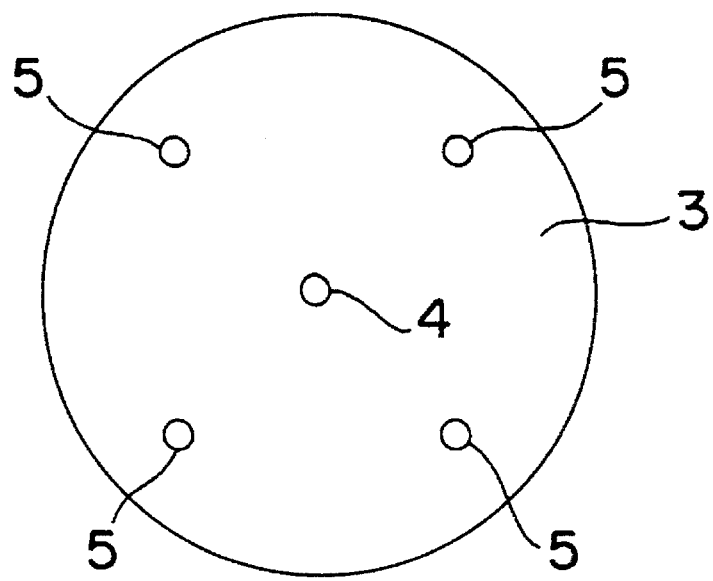
FIGS. 4, 5, 6 and 7 show various alternative electrode arrangements.
Figure 5:
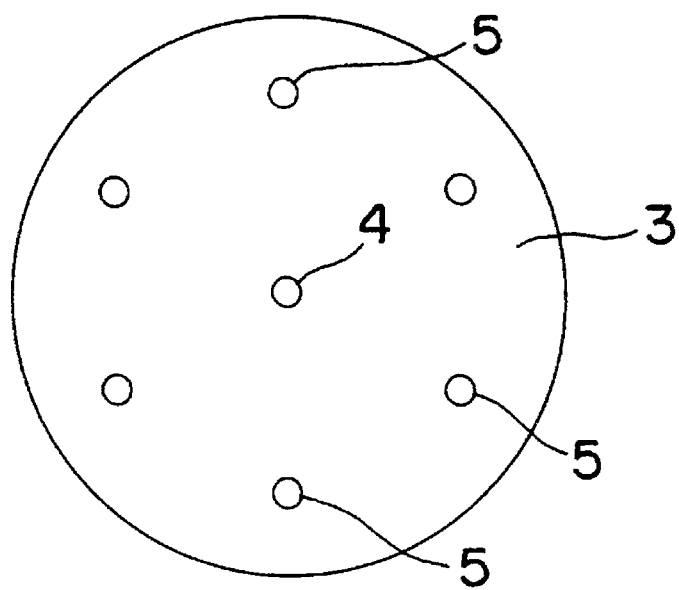

FIGS. 4 and 5 show alternative counter-electrode arrangements, where in each case a pin-shaped central electrode 4 spring-mounted in the electrode carrier 3 is surrounded by four or six similarly pin-shaped counter-electrodes 5, respectively.

Figure 6:
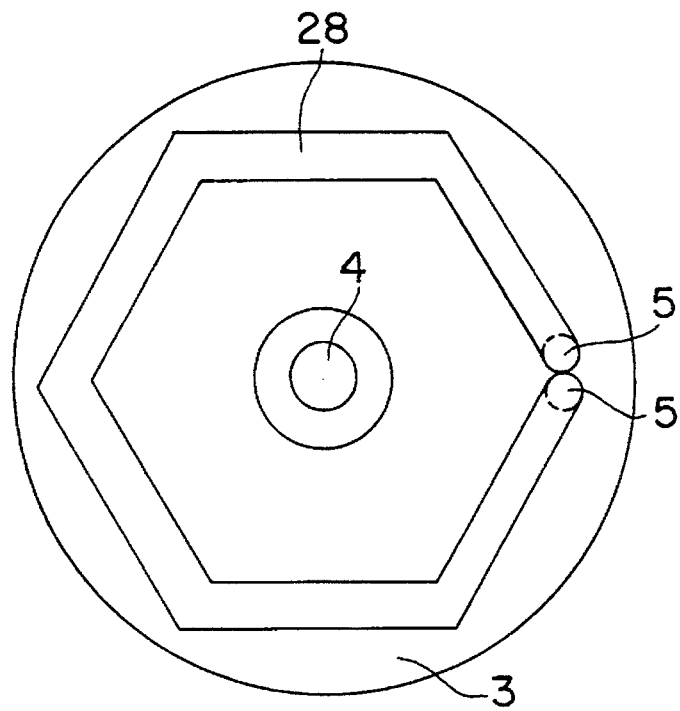
Figure 7:
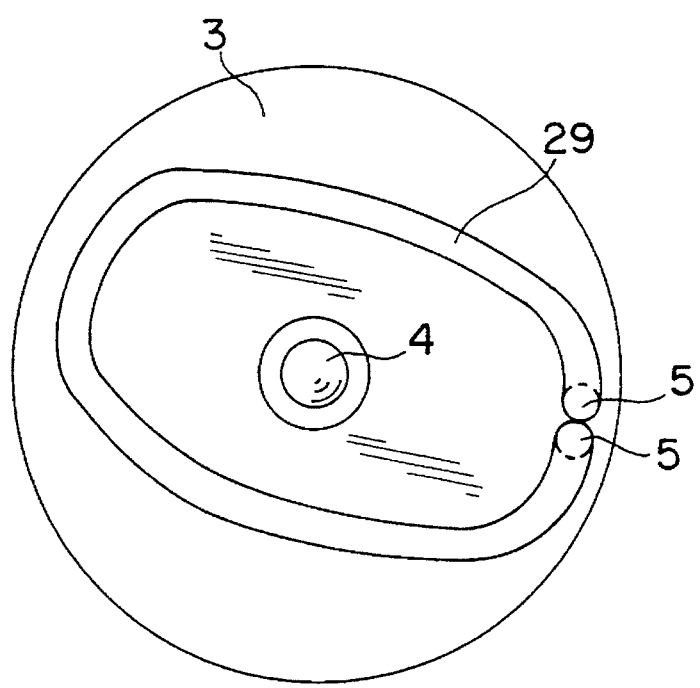

FIGS. 6 and 7 likewise show alternative counter-electrode arrangements, with the counter-electrode arranged as a wire ring in the shape of a polygon and an ellipse, respectively.

FIG. 8 shows the device with the DC power source (2), battery test means and switch (12), battery charge "OK" indicator light (10), polarity-reversing switch (18), operation indicator light (9), operating voltage adjusting means and switch (13) and cylindrical counter-electrode (30), as well as electrical connections from the power source through the various switches, etc., to the electrode and counter-electrode (note that between the polarity-reversing switch and the electrode and counter-electrode the indicated polarity is subject to being reversed from the depicted designations).

FIG. 9 shows an embodiment with a pen-shaped cylindrical housing part (6) containing the electrode carrier (3) being separate and electrically connected to the housing (1) by a flexible cable (20) (note that the indicated polarity is subject to being reversed).

We claim:

1. A device for treating inflammatory skin changes in the initial stage, said device comprising a housing, with a direct-current source and a switch for interrupting the flow of said current fitted therein, and an electrode carrier on which are arranged an electrode and at least one counter-electrode, which electrode is connected electrically to one pole of the direct-current source, and which counter-electrode is electrically connected to the opposite pole of the direct-current source, said device characterized in that the electrode is pin-shaped and concentrically surrounded by the one or more counter-electrodes, the electrode carrier being mounted movably on a first spring in a cylindrical housing part, and electrode being mounted on a second spring inside the electrode carrier, the restoring force of which second spring is less than that of the first spring, the electrode and one or more counter-electrodes being in the operating state of the device, brought to bear on the area of skin which is to be treated.

2. Device according to claim 1, wherein the direct-current source is a battery and the housing additionally comprises a switch and control unit with means for checking the charge state of the battery and the operating state of the device, and also means for adjusting the operating voltage.

3. Device according to claim 2, wherein the means for adjusting the operating voltage is a change-over switch with which the operating voltage can be preset to 9 or 18 V.

4. Device according to claim 2, wherein the means for adjusting the operating voltage permits a continuous adjustment of the operating voltage between 3 and 18 V.

5. Device according to claim 1, wherein the electrode and one or more counter-electrodes are made of materials selected from the group consisting of corrosion-resistant steel, noble metals and alloys of noble metals.

6. Device according to claim 5, wherein the counter-electrode is arranged parallel to the electrode and consists of a wire bent at a right-angle and shaped as a wire loop which concentrically surrounds the inner pin electrode.

7. Device according to claim 6, wherein the wire loop has shape chosen from the group consisting of a circle, an ellipse and a polygon.

8. Device according to claims 7, wherein the wire loop is sized such that the smallest circle which can fully contain it has a diameter of 5–15 mm.

9. Device according to claim 5, wherein the counter-electrode is cylindrically shaped and concentrically surrounds the electrode.

10. Device according to claim 9, wherein the cylindrical counter-electrode has a diameter of 5–15 mm.

11. Device according to claim 5, wherein there is a plurality of counter-electrodes, arranged to concentrically surround the electrode.

12. Device according to claim 8, wherein the distance between the counter-electrodes and the electrode (4) is 5–15 mm.

13. Device according to claim 8, wherein the electrode and counter-electrodes have a diameter of 0.5–2 mm.

14. Device according to claim 13, wherein the electrode carrier can be pushed into the cylindrical housing part by overcoming the restoring force of the first spring, as a result of which a switch is activated, closing the current to the electrode and counter-electrodes.

15. Device according to claim 14, wherein, for simple replacement of the electrode carrier, the cylindrical housing part is subdivided into a top part and a bottom part which are provided in each case with corresponding threads and are screwed together.

16. Device according to claim 15, wherein the direct-current source is a battery and the housing additionally comprises a switch and control unit with means for checking the charge state of the battery and the operating state of the device, and also means for adjusting the operating voltage, and wherein the switch and control unit additionally comprises a means for reversing the polarity of the current flowing to the counter-electrodes and the electrode.

17. Device according to claim 16, wherein the cylindrical housing part is integrated in the housing.

18. Device according to claim 16, wherein the cylindrical housing part is of pen-shaped design and is connected electrically to the housing via a flexible cable.

19. Method for treating inflammatory skin changes in the initial stage by moistening the affected area of skin with a physiologically tolerated electrolyte solution, placing the electrodes of the device according to claim 1 on to the moistened area of skin, and switching on the current flow.

20. Method according to claim 19, wherein the electrolyte solution is chosen from the group consisting of water, saliva and a physiological saline solution.

* * * * *

UNITED STATES PATENT AND TRADEMARK OFFICE
CERTIFICATE OF CORRECTION

PATENT NO.: 5,470,349

DATED: November 28, 1995

INVENTOR(S): KLEDITSCH et al.

It is certified that error appears in the above-identified patent and that said Letters Patent is hereby corrected as shown below:

Column 8, claim 12, "claim 8" should be --claim 11--.

Column 8, claim 13, "claim 8" should be --claim 11--.

Signed and Sealed this

Sixteenth Day of April, 1996

*Attest:*

BRUCE LEHMAN

*Attesting Officer*           Commissioner of Patents and Trademarks